United States Patent
Kim et al.

(10) Patent No.: US 9,421,244 B2
(45) Date of Patent: *Aug. 23, 2016

(54) LONG-ACTING INTERFERON BETA FORMULATION COMPRISING AN IMMUNOGLOBULIN FRAGMENT

(75) Inventors: Dae Jin Kim, Hwaseong-si (KR); Min Young Kim, Suwon-si (KR); Jin Sun Kim, Yongin-si (KR); Sung Hee Hong, Suwon-si (KR); Sung Youb Jung, Suwon-si (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/638,821

(22) PCT Filed: Apr. 4, 2011

(86) PCT No.: PCT/KR2011/002335
§ 371 (c)(1),
(2), (4) Date: Oct. 1, 2012

(87) PCT Pub. No.: WO2011/122923
PCT Pub. Date: Oct. 6, 2011

(65) Prior Publication Data
US 2013/0028867 A1 Jan. 31, 2013

(30) Foreign Application Priority Data
Apr. 2, 2010 (KR) .................. 10-2010-0030577

(51) Int. Cl.
*A61K 38/21* (2006.01)
*A61K 47/48* (2006.01)
*C07K 14/565* (2006.01)
*C07K 19/00* (2006.01)

(52) U.S. Cl.
CPC ......... *A61K 38/215* (2013.01); *A61K 47/48369* (2013.01); *A61K 47/48423* (2013.01); *A61K 47/48507* (2013.01); *C07K 14/565* (2013.01); *C07K 19/00* (2013.01); *C07K 2317/52* (2013.01); *C07K 2317/732* (2013.01); *C07K 2317/734* (2013.01); *C07K 2319/30* (2013.01)

(58) Field of Classification Search
CPC .............. A61K 38/215; C07K 14/565; C07K 2319/30; C07K 19/00
See application file for complete search history.

(56) References Cited

U.S. PATENT DOCUMENTS

| | | | |
|---|---|---|---|
| 5,908,626 A | 6/1999 | Chang et al. | |
| 7,527,946 B2 | 5/2009 | Whitty et al. | |
| 2004/0115168 A1* | 6/2004 | DeFrees et al. | 424/85.6 |
| 2004/0126361 A1* | 7/2004 | Saifer et al. | 424/85.6 |
| 2006/0228332 A1* | 10/2006 | Gillies et al. | 424/85.6 |
| 2006/0269553 A1* | 11/2006 | Kim et al. | 424/155.1 |
| 2007/0041967 A1* | 2/2007 | Jung et al. | 424/133.1 |
| 2009/0208454 A1* | 8/2009 | Kraynov et al. | 424/85.6 |

FOREIGN PATENT DOCUMENTS

| | | |
|---|---|---|
| JP | 2007-536211 A | 12/2007 |
| KR | 10-1999-0075253 A | 10/1999 |
| KR | 10-2004-0085287 A | 10/2004 |
| KR | 10-2005-0047032 A | 5/2005 |
| KR | 100541850 B1 | 1/2006 |
| WO | 96/32478 | 10/1996 |
| WO | 97/34631 | 9/1997 |
| WO | 99/55377 A2 | 11/1999 |
| WO | 01/03737 A1 | 1/2001 |
| WO | 2004/020405 A2 | 3/2004 |
| WO | 2005/047334 A1 | 5/2005 |

OTHER PUBLICATIONS

Mickle J.E. et al. Genotype-phenotype relationships in cystic fibrosis. Med. Clin. North Am., 2000, vol. 84(3), p. 597-607.*
Wells, J.A. Additivity of mutational effects in proteins. Biochemistry, 1990, vol. 29(37), p. 8509-8517.*
Goldstein, D., et al. The role of interferon in cancer therapy: A currenet perspective. CA Cancer J. Clin., 1988, vol. 38, p. 258-277.*
Goodkin, D.E. Role of steroids and immunosuppression and effects of interferon beta-1b in multiple sclerosis. West J. Med, 1994, vol. 161, p. 292-298.*
Pepinksy et al., "Improved Pharmacokinetic Properties of a Polyethylene Glycol-Modified Form of Interferon-beta-1a with Preserved in Vitro Bioactivity," The Journal of Pharmacology and Experimental Therapeutics, 2001, vol. 297, No. 3, pp. 1059-1066.
Kim et al., "Serum Immunoglobulin Fused Interferon-alpha Inhibited Tumor Growth in Athymic Mice Bearing Colon 26 Adenocarcinoma Cells," J. Vet. Sci., 2008, vol. 9, No. 1, pp. 45-50.
Chapman et al., "PEGylated Antibodies and Antibody Fragments for Improved Therapy: A Review," Advanced Drug Delivery Reviews, 2002, pp. 531-545.
Korean Patent Office, Korean Office Action issued in corresponding KR Application No. 10-2011-0030869, dated Feb. 25, 2013.
European Patent Office, Search report issued in European Patent Application No. 11763095.4 dated Dec. 10, 2013.
Japanese Patent Office, Office Action issued in Japanese Patent Application No. 2013-502502 dated Feb. 4, 2014.
Yamazaki, N. "Interferon Therapy of Malignant Melanoma" Biotherapy, Japanese Journal of cancer and Chemotherapy Publishers Inc., 2000, pp. 139-144, vol. 14 (2).

(Continued)

*Primary Examiner* — Robert Landsman
*Assistant Examiner* — Bruce D Hissong
(74) *Attorney, Agent, or Firm* — Sughrue Mion, PLLC

(57) ABSTRACT

The present invention relates to a long-acting interferon beta formulation having improved in vivo duration and stability, comprising an interferon beta conjugate that is prepared by covalently linking interferon beta with an immunoglobulin Fc region via a non-peptidyl polymer, and a preparation method thereof. The long-acting interferon beta formulation of the present invention maintains in vivo activity of interferon beta at a relatively high level and remarkably increases the serum half-life thereof, thereby being used for various diseases, for which interferon is efficacious.

20 Claims, 5 Drawing Sheets

(56) References Cited

OTHER PUBLICATIONS

Takane, H et al. "Influence of administering timing on antitumor effect of interferon-β intended for mice" Clinical Pharmacology and Therapeutics, 2000, pp. 441-442, vol. 31 (2).

Hara, M; "Basic research on injection treatment of interferon for urinary bladder cavity to urinary bladder tumor" Japanese Journal of Urology. 1989, pp. 158-166, vol. 80 (2).

Jacobs, L et al. Intramuscular Interferon Beta-1a for Disease Progression in relapsing multiple sclerosis: Annual Neurology, 1996, pp. 285-294, vol. 39 (3).

Kohriyama, T et al. "IFNβ treatment for multiple sclerosis and predictive factor for effect" Japanese Journal of Clinical medicine, 2008, pp. 1119-1126, vol. 66 (6).

Japanese Patent Office, Communication dated Jan. 27, 2015 issued in corresponding Japanese application No. 2013-502502.

* cited by examiner 1. non-reducing conditions 1. non-reducing conditions

LONG-ACTING INTERFERON BETA FORMULATION COMPRISING AN IMMUNOGLOBULIN FRAGMENT

CROSS REFERENCE TO RELATED APPLICATIONS

This application is a National Stage of International Application No. PCT/KR2011/002335 filed Apr. 4, 2011, claiming priority based on Korean Patent Application No. 10-2010-0030577 filed Apr. 2, 2010, the contents of all of which are incorporated herein by reference in their entirety.

TECHNICAL FIELD

The present invention relates to a long-acting interferon beta formulation having improved in vivo duration and stability, comprising an interferon beta conjugate that is prepared by covalently linking interferon beta with an immunoglobulin Fc region via a non-peptidyl polymer, and a preparation method thereof. The invention provides method for treating in a subject having a viral infections, autoimmune diseases, cancer, or degenerative disorders of the nervous system. The long-acting interferon beta formulation of the present invention maintains in vivo activity of interferon beta at a relatively high level and remarkably increases the serum half-life thereof.

BACKGROUND ART

Interferon beta is known as a substance that has an antiviral activity and suppresses cell proliferation, and also has the functions of anti-proliferation, augmentation of the cytotoxicity of lymphocytes, nature immune regulation, macrophage activation, enhancement of cytotoxic T cell responses, and enhancement of macrophage activity, and can be used for the treatment of viral infections, autoimmune diseases, and cancer. Currently, three forms of human recombinant interferon beta have been approved by US and European regulatory authorities for the treatment of multiple sclerosis; one type of non-glycosylated serine17-interferon-beta-1b produced from a strain of *Escherichia coli* and two types of glycosylated interferon-beta-1a produced from mammalian cells.

Betaseron is the brand name for non-glycosylated serine17-interferon-beta-1b produced from a strain of *Escherichia coli*, and is given every other day at a high dose of 250 µg. Avonex (Biogen, Inc.) is the brand name for glycosylated interferon-beta-1a produced from mammalian cells, and is given once a week by intramuscular injection, and it's approval was followed by approval of Rebif (Serono, Inc.). Even though Rebif is similar to Avonex and should be given three times a week, it was approved because of differences in the efficacy and formulation.

Non-glycosylated interferon is problematic in that it is very unstable, and thus precipitation occurs due to increased sensitivity to thermal denaturation and hydrophobic aggregation. Meanwhile, glycosylated interferon has a relatively long half-life in the body, compared to non-glycosylated interferon, and the half-life is prolonged from two days (intravenous injection) to one week (intramuscular injection), depending on its route of administration. However, diseases for which interferon-beta is efficacious require chronic management, and thus a long-acting formulation capable of acting one week or longer is demanded to solve the problem of interferon-beta instability. Therefore, many efforts have been made to improve the serum stability of interferon-beta and maintain the drugs in the blood at high levels for a prolonged period of time, thereby maximizing the pharmaceutical efficacy of the drugs. These long-acting interferon-beta formulations need to increase the stability of interferon-beta and maintain the titers at sufficiently high levels without causing immune responses in patients.

To stabilize interferon-beta and prevent hydrophobic aggregation, a polymer having high solubility, such as polyethylene glycol (PEG), was conventionally used to chemically modify the surface of a peptide. By binding to specific regions of the target interferon-beta, PEG increases the molecular weight of a peptide to prevent clearance by the kidneys and aggregation and thus improves the stability to increase the in vivo half-life, without causing serious side effects. For example, WO99/55377 discloses that PEG with a size of 20 KDa is linked to the sulfhydryl group (—SH) of cysteine residue in interferon beta-1a to improve the solubility and stability at neutral pH (reduced aggregation) and to reduce immunogenicity. U.S. Pat. No. 0,962,978 B2 discloses that PEG with a size of 20, 30, or 40 KDa is linked to the N-terminus of interferon beta-1a. In addition, US 2004/0126361 discloses that PEG with a size of 10 or 30 KDa is linked to the N-terminus of interferon beta-1b. These methods increase the molecular weight of PEG to prolong the in vivo duration of a peptide drug, whereas the increased molecular weight remarkably reduces titer of the peptide drug and reactivity to interferon beta, leading to a reduction in the yield and an increase in production costs.

U.S. Pat. No. 5,908,626 describes a fusion protein of interferon beta 1a and (γ4) Fc via a peptide linker, WO200103737 describes a fusion protein of interferon beta 1a and IgG1Fc, IgG4Fc, or IgG1CH. In US600735 B2, a direct fusion of interferon beta 1a and IgG1Fc fragment is compared with a fusion via G4S linker. US20060228332 describes a fusion protein of interferon beta 1a and immunoglobulin fragment (Fc), and WO2004020405 describes a fusion protein of interferon beta and non-glycosylated transferrin (mTf). These fusion proteins are advantageous in that low pegylation yield and non-specificity can be overcome, whereas they are disadvantageous in that the serum half-life is not increased as expected, and in some cases, titer becomes low. To maximize the increase in the serum half-life, various types of peptide linkers have been used, but they may cause immune responses.

Other attempts have been made. US20040115168A1 describes glycopegylation of linking a sugar chain of interferon beta-1a with PEG, but a low pegylation yield is problematic, and Korea Patent No. 10-0541850 describes a method of adding one or more sugar chains, in which interferon beta-1a variants are used to perform partial substitution of amino acid at position 7, but the amino acid substitution of native form may generate a problem in the in vivo stability.

DISCLOSURE

Technical Problem

Accordingly, the present inventors have used a method of site-selectively linking an immunoglobulin Fc region, a non-peptidyl polymer, and interferon beta with each other by a covalent bond in order to improve the serum half-life of interferon beta and to maximize in vivo activity thereof at the same time. As a result, the serum half-life of interferon beta conjugate was remarkably increased, which is more excellent than the known pegylation of interferon beta. Further, non-glycosylated interferon beta 1b-Fc conjugate which has the problems of low solubility and high dose but has advantages of easy production process and low production costs was found to show the serum half-life and titer being similar to or higher than the glycosylated interferon beta 1a-Fc conjugate.

Technical Solution

It is an object of the present invention to provide an excellent long-acting interferon beta formulation that maintains in vivo activity of interferon beta and remarkably increases the serum half-life thereof, and a preparation method thereof.

Advantageous Effects

The interferon beta conjugate of the present invention maintains in vivo activity of a peptide at a relatively high level and remarkably increases the serum half-life thereof.

BEST MODE

Figure 1:
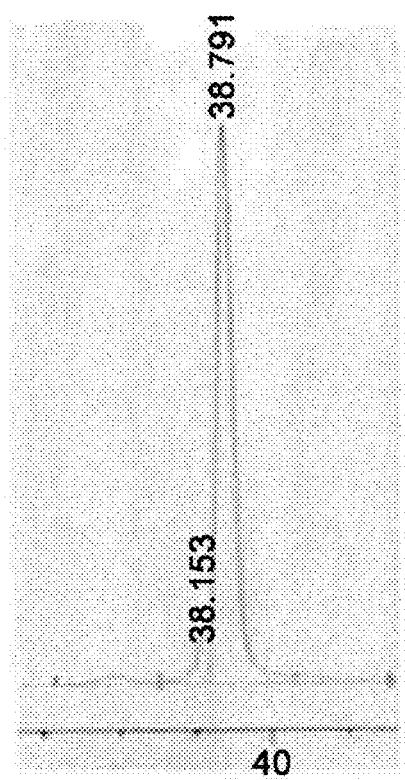
FIG. 1 is the result of RP HPLC of interferon beta 1b-PEG-immunoglobulin Fc conjugate.
Figure 2:
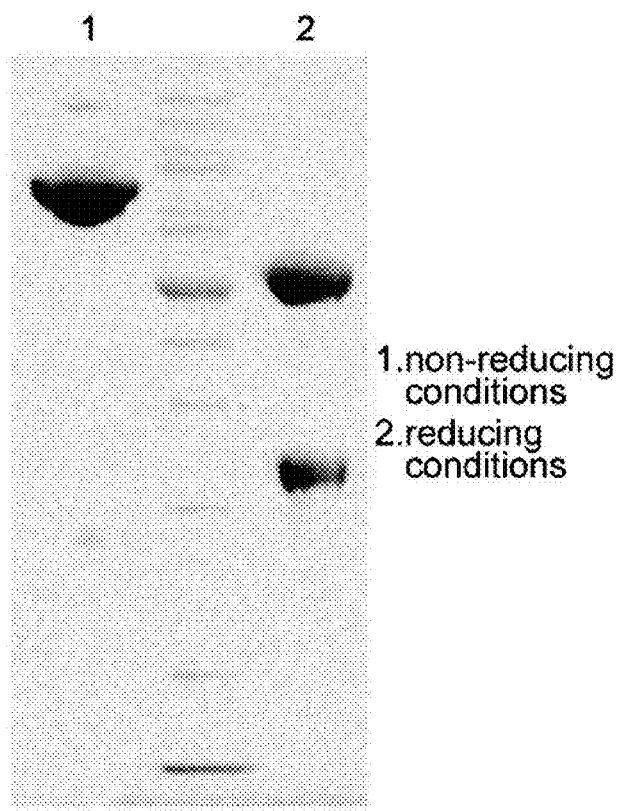
FIG. 2 is the result of 12% SDS-PAGE of interferon beta 1b-PEG-immunoglobulin Fc conjugate.
Figure 3:
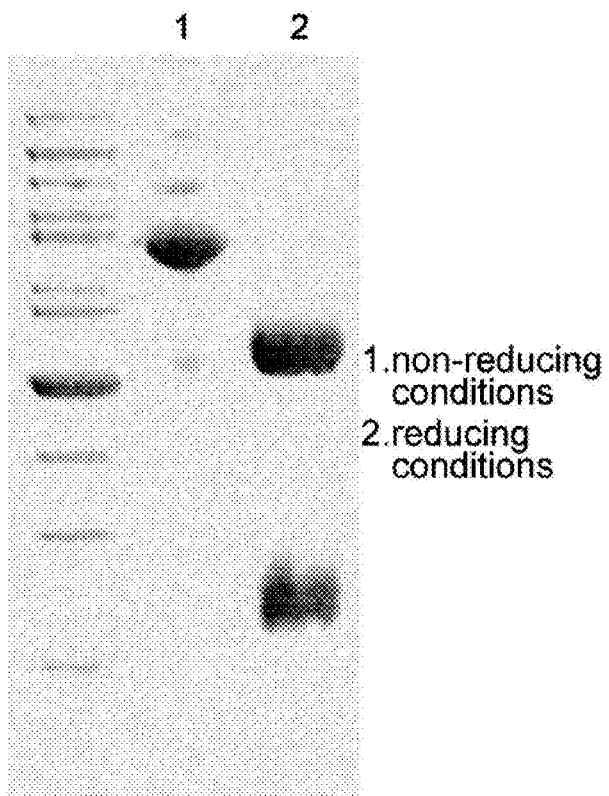
FIG. 3 is the result of 12% SDS-PAGE of interferon beta 1a-PEG-immunoglobulin Fc conjugate.
Figure 4:
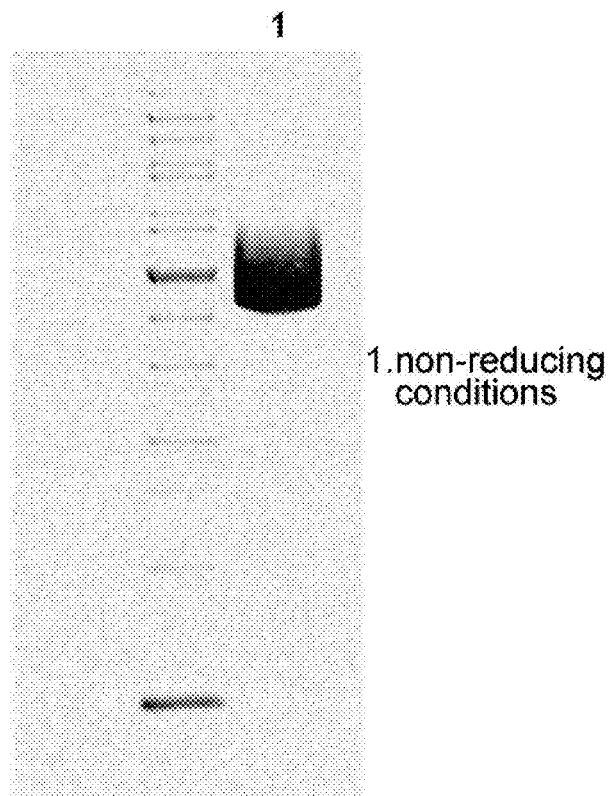
FIG. 4 is the result of 12% SDS-PAGE of interferon beta 1b-20 kDa PEG conjugate.
Figure 5:
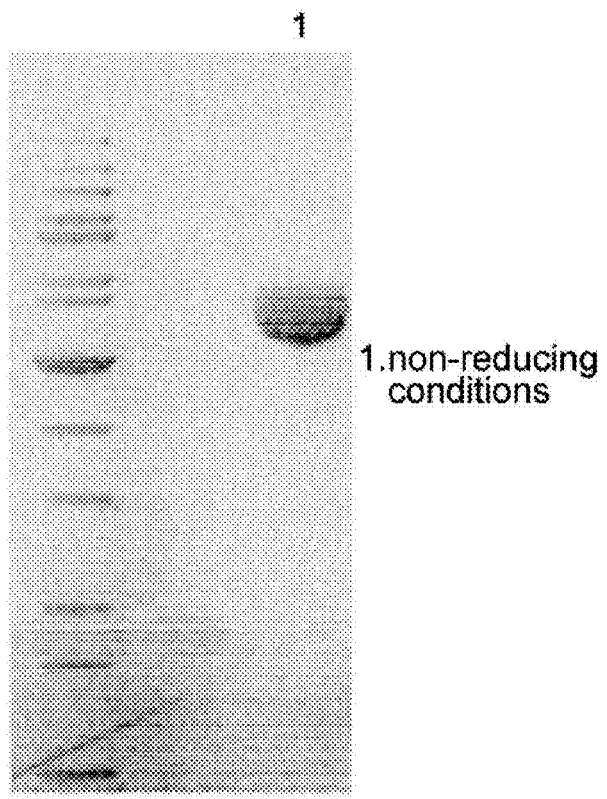
FIG. 5 is the result of 12% SDS-PAGE of interferon beta 1b-20 kDa PEG conjugate.

In one aspect to achieve the above objects, the present invention provides a long-acting interferon beta formulation having improved in vivo duration and stability, comprising an interferon beta conjugate that is prepared by covalently linking interferon beta with an immunoglobulin Fc region via a non-peptidyl polymer having two reactive terminal groups.

The interferon beta of the present invention is a protein that has an antiviral activity and suppresses cell proliferation, and also has the functions of anti-proliferation, augmentation of the cytotoxicity of lymphocytes, nature immune regulation, macrophage activation, enhancement of cytotoxic T cell responses, and enhancement of macrophage activity, and can be used for the treatment of viral infections, autoimmune diseases, cancer and multiple sclerosis. The interferon beta is preferably interferon beta 1b, interferon beta 1a or the like.

The interferon beta of the present invention may be preferably N-terminus-specific conjugate. The present inventors demonstrated that it binds to the N-terminus so as to improve the activity.

The term "activity", as used herein, means that interferon beta exhibits its function through binding to the interferon beta receptor.

Such N-terminus-specific conjugation can be achieved by pH control, and preferably, in the range from 4.5 to 7.5.

The term "N-terminus", as used herein, can be used interchangeably with "N-terminal region".

The immunoglobulin Fc region used in the preparation of long-acting interferon beta is safe for use as a drug carrier because it is a biodegradable polypeptide that is in vivo metabolized. Also, the immunoglobulin Fc region has a relatively low molecular weight, as compared to whole immunoglobulin molecules, and thus it is advantageous in the preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic.

The term "immunoglobulin Fc region", as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, it may be a fragment having a deletion in a relatively long portion of the amino acid sequence of CH2 and/or CH3. That is, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

Further, the immunoglobulin Fc region of the present invention includes a sequence derivative (mutant) thereof as well as a native amino acid sequence. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. In addition, other various derivatives are possible, including derivatives having a deletion of a region capable of forming a disulfide bond, a deletion of several amino acid residues at the N-terminus of a native Fc form, or an addition of methionine residue to the N-terminus of a native Fc form. Furthermore, to remove effector functions, a deletion may occur in a complement-binding site, such as a C1q-binding site and an ADCC site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions.

The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to that of the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size-exclusion chromatography to isolate Fc or pF'c.

Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation", as used herein, means to enzymatically remove sugar moieties from an Fc region, and the term "aglycosylation" means that an Fc region is produced in an unglycosylated form by a prokaryote, preferably E. coli.

In addition, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-life of ligand-binding proteins.

The term "combination", as used herein, means that polypeptides encoding single-chain immunoglobulin Fc regions of the same origin are linked to a single-chain polypeptide of a different origin to forma dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations or hybrids thereof. Preferred are IgG2 and IgG4 subclasses, and most preferred is the Fc region of IgG4 rarely having effector functions such as CDC (complement dependent cytotoxicity).

As the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The term "non-peptidyl polymer", as used herein, refers to a biocompatible polymer including two or more repeating units linked to each other by any covalent bond excluding a peptide bond.

The non-peptidyl polymer which can be used in the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof, and preferably, polyethylene glycol. The derivatives thereof well known in the art and being easily prepared within the skill of the art are also included in the scope of the present invention.

The peptide linker which is used in the fusion protein obtained by a conventional inframe fusion method has drawbacks that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without any limitation, as long as it is a polymer having the aforementioned function, that is, a polymer having resistance to the in-vivo proteolytic enzyme. The non-peptidyl polymer has a molecular weight in the range of 1 to 100 kDa, more preferably 1 to 90 kDa, more preferably 1 to 80 kDa, more preferably 1 to 70 kDa, more preferably 1 to 60 kDa, more preferably 1 to 50 kDa, more preferably 1 to 40 kDa, more preferably 1 to 30 kDa, and most preferably of 1 to 20 kDa. The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group as two or three reactive terminal groups, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0.

The two reactive terminal groups of the non-peptidyl polymer may be the same as or different from each other. For example, the non-peptide polymer may possess a maleimide group at one end and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the protein conjugate of the present invention.

The long-acting formulation of the present invention has an excellent effect of maintaining in vivo duration and stability.

In accordance with the specific Example of the present invention, the long-acting interferon beta formulation of the present invention has an approximately 10 fold-increase in the half-life, compared to the native interferon beta (Table 1).

The long-acting formulation of the present invention may be administered via any of the common routes, as long as interferon beta is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the long-acting formulation may be administered in an injectable form. In addition, the long-acting formulation of the present invention may be administered using a certain apparatus capable of transporting the active ingredients into a target cell.

The long-acting formulation comprising the conjugate of the present invention may comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The long-acting formulation of the present invention may be formulated into a variety of dosage forms in combination with the aforementioned pharmaceutically acceptable carriers. For example, for oral administration, the long-acting formulation may be formulated into tablets, troches, capsules, elixirs, suspensions, syrups or wafers. For injectable preparations, the long-acting formulation may be formulated into single-dose ampule or multidose container. The long-acting formulation may be also formulated into solutions, suspensions, tablets, pills, capsules and sustained release preparations.

Examples of the carrier, the excipient, and the diluent suitable for the formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oils. In addition, the formulations may further include fillers, anti-coagulating agents, lubricants, humectants, perfumes, and antiseptics.

The long-acting formulation of the present invention can be determined by several related factors including the types of diseases to be treated, administration routes, the patient's age, gender, weight and severity of the illness, as well as by the types of the drug as an active component. Since the long-acting formulation of the present invention has excellent in vivo duration and titer, it can remarkably reduce the administration frequency and dose of long-acting formulation of the present invention.

The long-acting formulation of the present invention improves in vivo duration and stability of interferon beta, and thus can be effectively used for the treatment or prevention of disease selected from the group consisting of viral infections, autoimmune diseases, cancer, and degenerative disorders of the nervous system.

The cancer includes ovarian cancer, breast cancer, uterine cancer, prostate cancer, testicular cancer, lung cancer, leukemia, lymphoma, melanoma, colon cancer, bladder cancer, renal cancer, stomach cancer, pancreatic cancer, head and neck cancer, skin cancer, neuroma, carcinoma, sarcoma, adenoma and myeloma.

The degenerative diseases of the nervous system include multiple sclerosis, more particularly, relapsing remitting, primary progressive, and secondary progressive multiple sclerosis.

In another aspect, the present invention provides a method for preparing a long-acting interferon beta formulation, comprising the steps of:

(1) covalently linking a non-peptidyl polymer having a reactive group of aldehyde, maleimide, or succinimide derivatives at both ends thereof, with an amine group or thiol group of interferon beta;

(2) isolating a conjugate from the reaction mixture of (1), in which the conjugate comprises interferon beta covalently linked with the non-peptidyl polymer at a site other than the N-terminus; and (3) covalently linking an immunoglobulin Fc to the other end of the non-peptidyl polymer of the isolated conjugate to produce a conjugate comprising the immunoglobulin Fc region and interferon beta, which are linked to each end of the non-peptidyl polymer.

In still another aspect, the present invention provides a method for treating a subject having a viral infections, autoimmune diseases, cancer, or degenerative disorders of the nervous system, comprising of administering to the subject an effective amount of the long-acting formulation.

As used herein, a subject can be a mammal, for example, human, a non-human primate, a horse, a sheep, a cat, a dog, a cow or a pig.

MODE FOR INVENTION

Hereinafter, a better understanding of the present invention may be obtained through the following Examples which are set forth to illustrate, but are not to be construed as the limit of the present invention.

Example 1

Purification of Pegylated Interferon Beta 1b

Interferon beta 1b (Hanmi-interferon beta 1b) produced by the present inventor was prepared at a concentration of 1 mg/mL, and for pegylation of interferon beta at its N-terminus, 3.4 kDa PropionylALD2 PEG was added at a molar ratio of interferon and PEG of 1:15 and completely dissolved. Thereafter, 20 mM NaCNBH3 as a reducing agent was added thereto, and reacted at room temperature for 90 min. Then, the reaction mixture was diluted 10-fold with 50 mM potassium phosphate containing 0.05% zwitergent 3-14 detergent (pH 6.0), and applied to a SP HP column (Hitrap 5 mL, GE Healthcare). The SP HP column was equilibrated with 20 mM potassium phosphate containing 0.05% zwitergent 3-14 detergent (pH 6.0), and the flow rate was 5 mL/min. For the purification of mono-pegylated interferon, 20 mM potassium phosphate containing zwitergent 3-14 detergent (pH 6.0) and 1 M NaCl were applied from 0 to 40% with 40 column volumes to purify the mono-pegylated interferon beta 1b.

Example 2

Preparation of Interferon Beta 1b-Immunoglobulin Fc Conjugate

The pegylated interferon beta 1b obtained in Example 1 was coupled with an immunoglobulin Fc. The reaction was performed at a molar ratio of interferon beta:immunoglobulin Fc of 1:10 and a total concentration of protein of 50 mg/ml at 4° C. for 16 hours. At this time, 20 mM NaCNBH3 as a reducing agent was added thereto. Then, the reaction mixture was diluted 15-fold with 50 mM potassium phosphate containing 0.05% zwitergent 3-14 detergent (pH 6.0), and applied to a SP HP column (Hitrap 5 mL, GE Healthcare). The SP HP column was equilibrated with 20 mM potassium phosphate containing 0.05% zwitergent 3-14 detergent (pH 6.0), and the flow rate was 5 mL/min. For the elution of coupled protein, 20 mM potassium phosphate containing 0.05% zwitergent 3-14 detergent (pH 6.0) and 1 M NaCl were applied by a linear gradient from 0 to 40% with 40 column volumes. The SP HP column was used to remove unreacted immunoglobulin Fc. The coupling protein solution eluted from the SP HP column was diluted 20-fold with 20 mM Tris-HCl containing 0.05% zwitergent 3-14 detergent (pH 8.0), and applied to a Q HP column (Hitrap 5 mL, GE Healthcare). The Q HP column was equilibrated with 20 mM Tris-HCl containing 0.05% zwitergent 3-14 (pH 8.0), and the flow rate was 5 mL/min. For the purification of interferon beta-PEG-immunoglobulin Fc, 20 mM Tris-HCl containing 0.05% zwitergent 3-14 (pH 8.0) and 1 M NaCl were applied by a linear gradient from 0 to 40% with 40 column volumes. The interferon beta 1b-immunoglobulin Fc conjugate purified from the Q HP column was analyzed by RP-HPLC, and the results are shown in FIG. 1

Example 3

Purification of Pegylated Interferon Beta 1a

For pegylation of interferon beta 1a (GEMA Biotech), the buffer composition was changed to 50 mM potassium phosphate containing 0.05% zwitergent 3-14 detergent (pH 6.0) and 100 mM NaCl. The interferon beta 1a was prepared at a concentration of 1 mg/mL, and for pegylation of interferon beta at its N-terminus, 3.4 kDa butyrALD2 PEG was added at a molar ratio of interferon and PEG of 1:20 and completely dissolved. Thereafter, 20 mM NaCNBH3 as a reducing agent was added thereto, and reacted at room temperature for 90 min. Then, the reaction mixture was diluted 10-fold with 20 mM potassium phosphate containing 0.05% zwitergent 3-14 detergent (pH 6.0), and applied to a SP HP column (Hitrap 5 mL, GE Healthcare). The SP HP column was equilibrated with 20 mM potassium phosphate containing 0.05% zwitergent 3-14 detergent (pH 6.0), and the flow rate was 5 mL/min. For the purification of mono-pegylated interferon, 20 mM potassium phosphate containing zwitergent 3-14 detergent (pH 6.0) and 1 M NaCl were applied from 0 to 40% with 40 column volumes for purification. After reaction of 3.4 kDa PropionylALD2 PEG with interferon beta 1a, the mono-pegylated interferon beta was purified.

Example 4

Preparation of Interferon Beta 1a-Immunoglobulin Fc Conjugate

The mono-pegylated interferon beta purified in Example 3 was coupled with an immunoglobulin Fc. The reaction was performed at a molar ratio of interferon beta:immunoglobulin Fc of 1:50 and a total concentration of protein of 50 mg/ml at room temperature for 2 hours. At this time, 20 mM NaCNBH3 as a reducing agent was added thereto. Then, the reaction mixture was diluted 15-fold with 20 mM potassium phosphate containing 0.05% zwitergent 3-14 detergent (pH 6.0), and applied to a SP HP column (Hitrap 5 mL, GE Healthcare). The SP HP column was equilibrated with 20 mM potassium phosphate containing 0.05% zwitergent 3-14 detergent (pH 6.0), and the flow rate was 5 mL/min. For the elution of coupled protein, 20 mM potassium phosphate containing 0.05% zwitergent 3-14 detergent (pH 6.0) and 1 M NaCl were applied by a linear gradient from 0 to 40% with 40 column volumes. The SP HP column was used to remove unreacted immunoglobulin Fc. 2 M ammonium sulfate was added to the coupling protein solution eluted from the SP HP column with slow stirring to a final concentration of 1.5M ammonium sulfate, and then applied to a SOURCE ISO (1 ml, GE Healthcare) column. The SOURCE ISO column was equilibrated with 50 mM potassium phosphate (pH 6.0), 1.5 M ammonium sulfate buffer, and the flow rate was 3 mL/min. To elute the coupled protein, 50 mM potassium phosphate buffer was applied by a linear gradient from 0 to 100% with 90 column volumes for purification.

Example 5

Preparation of Interferon Beta 1b-20 kDa PEG

Hanmi-interferon beta 1b was prepared at a concentration of 1 mg/mL, and for pegylation of interferon beta at its N-terminus, 20 kDa PropionylALD PEG was added at a molar ratio of interferon and PEG of 1:15 and completely dissolved. As a pegylation buffer, 100 mM potassium phosphate containing 0.05% zwitergent 3-14 (pH 6.0) and 5 mM NaCl were used, and 20 mM NaCNBH3 as a reducing agent was added thereto, and reacted at room temperature for 90 min. Then, the reaction mixture was diluted 10-fold with 50 mM potassium phosphate containing 0.05% zwitergent 3-14 detergent (pH 6.0), and applied to a SP HP column (Hitrap 5 mL, GE Healthcare). The SP HP column was equilibrated with 20 mM potassium phosphate containing 0.05% zwitergent 3-14 detergent (pH 6.0), and the flow rate was 5 mL/min. For the purification of mono-pegylated interferon, 20 mM potassium phosphate containing zwitergent 3-14 detergent (pH 6.0) and 1 M NaCl were applied from 0 to 40% with 40 column volumes to purify the mono-pegylated interferon beta 1b.

Example 6

Preparation of Interferon Beta 1a-20 kDa

Interferon beta 1a (GEMA Biotech) was prepared at a concentration of 1 mg/mL, and for pegylation of interferon beta at its N-terminus, 20 kDa PropionylALD PEG was added at a molar ratio of interferon and PEG of 1:5 and completely dissolved in 50 mM sodium phosphate buffer (pH 6.5) containing 150 mM NaCl. 20 mM NaCNBH3 as a reducing agent was added thereto, and reacted at room temperature for 18 hrs. Then, the reaction mixture was concentrated, and applied to a Superdex75 column (120 mL, GE Healthcare). The column was equilibrated with 30 mM sodium phosphate buffer containing 150 mM NaCl (pH 6.5), and the flow rate was 1 mL/min to purify the mono-pegylated interferon beta 1a.

Example 7

Measurement of In Vivo Activity and PK of Long-Acting Interferon

In-vitro cell activity was measured to analyze the efficacy and pharmacokinetic parameters of long-acting interferon beta formulation. For the measurement of in-vitro activity of interferon beta, WISH cell (ATCC) was generally used to perform cytopathic effect assay. WISH cell was treated with varying concentrations of interferon beta and long-acting interferon beta test materials, and protection against vesicular stomatitis virus was determined as EC50 value to measure the in vitro activity.

In addition, the blood plasma was isolated from animals (normal S.D. rat) treated with interferon beta and long-acting formulation, and pharmacokinetic parameters were calculated by CPE assay in the same manner as the in vitro activity test.

TABLE 1

| Test material | Serum half-life (hr) | In vitro titer (%) |
| --- | --- | --- |
| Interferon beta 1a (Avonex) | N.D. | 100.0 |
| Interferon beta 1b (Betaseron) | N.D. | 16.8 |
| Interferon beta 1a (GEMA Biotech) | N.D. | 82.4 |
| Interferon beta 1a (GEMA Biotech)-Fc conjugate | 46.86 | 10.9 |
| Interferon beta 1a (GEMA Biotech)-20 KDa PEG | 24.28 | 13.5 |
| Hanmi-interferon beta 1b | 4.28 | 38.1 |
| Hanmi-interferon beta 1b-Fc conjugate | 41.21 | 40.2 |
| Hanmi-interferon beta 1b-20 KDa PEG | 19.54 | 30.1 |

Table 1 shows the in-vitro cell activity and serum half-life of each test material. Herein, their in-vitro cell activities were determined, based on the value of interferon beta 1a (Avonex), and the Hanmi-interferon beta 1b-Fc conjugate was found to have a titer being equivalent to or more than that of Hanmi-interferon beta 1b prior to preparation of the conjugate. Native interferon beta 1b was found to have T½ of 4.28 hrs, indicating a short serum half-life. The interferon beta 1b-Fc conjugate was found to have a lower serum half-life and higher titer than the interferon beta 1a-Fc conjugate. In addition, the interferon beta-Fc conjugate showed a longer serum half-life than the interferon beta-20 kDa PEG conjugate.

The invention claimed is:

1. A long-acting interferon beta formulation, comprising an interferon beta conjugate that is comprised of interferon beta linked to an immunoglobulin Fc region via polyethylene glycol (PEG) having a reactive propionyl aldehyde group at each end thereof,
    wherein the interferon beta is interferon beta 1b; and
    wherein the PEG is linked to the N-terminus of interferon beta 1b.

2. The long-acting interferon beta formulation according to claim 1, wherein each end of the PEG is linked to an amine group or thiol group of the immunoglobulin Fc region and interferon-beta, respectively.

3. The long-acting interferon beta formulation according to claim 1, wherein the immunoglobulin Fc region comprises the sequence of a native Fc immunoglobulin region.

4. The long-acting interferon beta formulation according to claim 1, wherein the immunoglobulin Fc region is aglycosylated.

5. The long-acting interferon beta formulation according to claim 1, wherein the immunoglobulin Fc region is comprised of one to four domains selected from the group consisting of CH1, CH2, CH3 and CH4 domains.

6. The long-acting interferon beta formulation according to claim 1, wherein the immunoglobulin Fc region is a dimer of the heavy-chain constant region and the light-chain constant region selected from the group consisting of CH1, CH2, CH3 and CH4 domains.

7. The long-acting interferon beta formulation according to claim 5, wherein the immunoglobulin Fc region further comprises a hinge region.

8. The long-acting interferon beta formulation according to claim 1, wherein the immunoglobulin Fc region is an Fc region derived from IgG, IgA, IgD, IgE, or IgM.

9. The long-acting interferon beta formulation according to claim 8, wherein each domain of the immunoglobulin Fc region is a domain hybrid of a different origin derived from an immunoglobulin selected from the group consisting of IgG, IgA, IgD, IgE, and IgM.

10. The long-acting interferon beta formulation according to claim 8, wherein the immunoglobulin Fc region is a dimer or a multimer comprised of single-chain immunoglobulins composed of domains of the same origin.

11. The long-acting interferon beta formulation according to claim 8, wherein the immunoglobulin Fc region is an IgG4 Fc region.

12. The long-acting interferon beta formulation according to claim 11, wherein the immunoglobulin Fc region is a human aglycosylated IgG4 Fc region.

13. The long-acting interferon beta formulation according to claim 1, wherein PEG has a molecular weight ranging from 1 kDa to 100 kDa.

14. The long-acting interferon beta formulation according to claim 1, wherein PEG has a molecular weight ranging from 1 kDa to 20 kDa.

15. The long-acting interferon beta formulation according to claim 1, wherein the formulation is for the treatment of multiple sclerosis.

16. The long-acting interferon beta formulation according to claim 15, wherein the multiple sclerosis is selected from the group consisting of relapsing remitting, primary progressive, and secondary progressive multiple sclerosis.

17. The long-acting interferon beta formulation according to claim 15, further comprising a therapeutic agent for multiple sclerosis.

18. The long-acting interferon beta formulation according to claim 1, wherein the formulation is for treating a cancer, said cancer being selected from the group consisting of ovarian cancer, breast cancer, uterine cancer, prostate cancer, testicular cancer, lung cancer, leukemia, lymphoma, melanoma, colon cancer, bladder cancer, renal cancer, stomach cancer, pancreatic cancer, head and neck cancer, skin cancer, neuroma, carcinoma, sarcoma, adenoma and myeloma.

19. A method for preparing the long-acting interferon beta formulation of claim 1, comprising the steps of:

(1) covalently linking a PEG having a reactive propionyl aldehyde group at each end thereof, to an amine group or thiol group of interferon beta;
(2) isolating a reaction product of step (1), wherein the reaction product comprises interferon beta covalently linked to PEG at the N-terminus; and
(3) covalently linking an immunoglobulin Fc to the other end of the PEG of the isolated reaction product to produce a interferon beta conjugate comprising the immunoglobulin Fc region and interferon beta that are linked to each end of the PEG wherein the interferon beta is interferon beta 1b.

20. A method for treating multiple sclerosis, comprising administering an effective amount of the long-acting formulation of claim 1 to a subject in need thereof.

* * * * *